United States Patent [19]

Amirav et al.

[11] Patent Number: 5,741,711
[45] Date of Patent: Apr. 21, 1998

[54] FLAME-BASED METHOD AND APPARATUS FOR ANALYZING A SAMPLE

[75] Inventors: Aviv Amirav, 58 Bialik Avenue, Ramat Hasharon, Israel; Nitzan Tzanani, Tel-Aviv, Israel

[73] Assignee: Aviv Amirav, Ramat Hasharon, Israel

[21] Appl. No.: 566,555

[22] Filed: Dec. 4, 1995

[30] Foreign Application Priority Data

Sep. 13, 1995 [IL] Israel ......................... 115287

[51] Int. Cl.$^6$ ............................. G01N 21/72; G01N 21/71
[52] U.S. Cl. ............................. 436/154; 427/54; 436/153; 436/155; 436/160; 436/161; 436/171; 436/172
[58] Field of Search ...................... 422/54; 436/153–155, 436/160, 161, 171–172

[56] References Cited

U.S. PATENT DOCUMENTS

| | | | |
|---|---|---|---|
| 2,991,158 | 7/1961 | Harley et al. | 422/54 |
| 3,455,144 | 7/1969 | Bradley | 422/54 X |
| 3,661,533 | 5/1972 | David et al. | 422/54 |
| 3,767,363 | 10/1973 | Hofmann | 422/54 |
| 3,840,341 | 10/1974 | Rogers | 422/54 X |
| 4,201,550 | 5/1980 | Noszticzius et al. | 422/54 |
| 4,271,022 | 6/1981 | Dixon et al. | 210/198.2 |
| 4,332,664 | 6/1982 | Noszticzius et al. | 204/266 |
| 5,037,518 | 8/1991 | Young et al. | 204/230 |
| 5,153,673 | 10/1992 | Amirav | 356/315 |
| 5,317,932 | 6/1994 | Westlake, III et al. | 73/864.73 |
| 5,342,494 | 8/1994 | Shane et al. | 204/252 |
| 5,398,559 | 3/1995 | Westlake, III et al. | 73/863.81 |
| 5,442,968 | 8/1995 | Westlake, III et al. | 73/863.23 |

FOREIGN PATENT DOCUMENTS

| | | |
|---|---|---|
| 0 417 647 | 3/1991 | European Pat. Off. |
| 422994 | 4/1991 | European Pat. Off. |
| 2311135 | 9/1973 | Germany ......... 422/54 |
| 136569 | 11/1986 | Poland. |
| 913222 | 3/1982 | U.S.S.R. .......... 422/54 |
| 1127078 | 9/1968 | United Kingdom. |
| 1 584 978 | 2/1981 | United Kingdom. |
| WO 93/16790 | 9/1993 | WIPO. |

OTHER PUBLICATIONS

K.A.Lyutfaliev *automat. Kontr.–Izmer. Prib.* 1973, 1, 12–14.
J.W. Shumar et al. *NASA Contract. Rep.* 1976, NASA–CR–150947.
V.I. Skvortsov et al. *Svar. Proizvod.* 1987, 3, 5–6.
J.K. Jacobsen *Anal. Chem.*1965, 37, 319–320.
R.S. Braman *Anal. Chem.* 1966, 38, 734–742.
J.E. Lovelock et al. *Anal. Chem.* 1970, 42, 969–973.
O. LaSota *Chem Listy* 1979, 73, 974–981.
E. Atar et al.*Anal. Chem.* 1991, 63, 2061–2064.
S. Cheskis et al.*Anal. Chem.* 1993, 65, 539–555.
Nitzan Tzanani et al. *Anal. Chem.* 1995, 67, 167–173.
A. Amirav et al.*Anal. Chem.* 1995, 67, 3305–3318.

*Primary Examiner*—Arlen Soderquist
*Attorney, Agent, or Firm*—McAulay Fisher Nissen Goldberg & Kiel, LLP

[57] ABSTRACT

A flame based method for analyzing a sample by introducing the sample into a combustible gas mixture, igniting the combustible gas mixture to produce a flame, and detecting a characteristic of the resulting flame to determine the identity and/or concentration of one or more chemical substances in the sample, wherein the combustible gas mixture is generated by water electrolysis. The same method is also utilizable for determining the identity and/or concentration of one or more chemical compounds in the sample. A flame based detector apparatus for analyzing a sample is also described. The apparatus includes an inlet for introducing combustible gases therein, a feeder for introducing the sample into combustible gases, an ignitor for igniting the combustible gases to produce a flame, a detector for detecting a characteristic of the resulting flame for determining the identity and/or concentration of one or more chemical substances in the sample, and a water electrolyser for generating combustible gases and for directing the gases to the inlet.

21 Claims, 5 Drawing Sheets

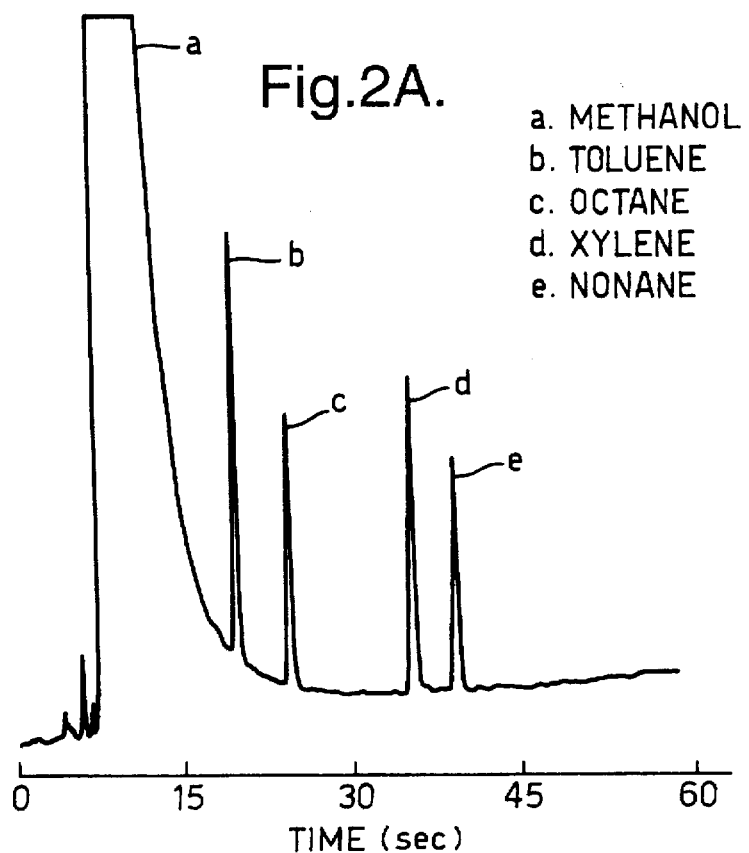
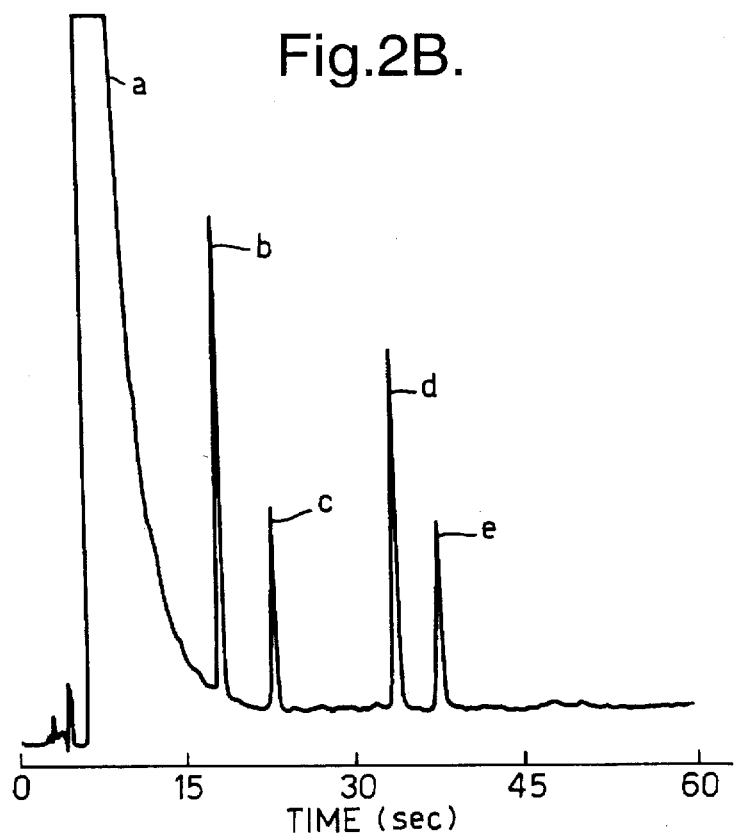

a. METHANOL
b. PYRIDINE
c. TOLUENE
d. THT
e. DMMP
f. NONANE
g. CHLOROTOLUENE

FLAME-BASED METHOD AND APPARATUS FOR ANALYZING A SAMPLE

The present invention relates to flame based analyzing methods and apparatus, and particularly to a method and detector apparatus for detecting the presence and/or concentration of one or more chemical substances therein by igniting a combustible gas mixture containing the sample to produce a flame, and detecting a characteristic of the resulting flame.

The Flame Ionization Detector (FID) is the most popular and widely used detector of Gas Chromatograph (GC) instruments. It is also used as a portable or stationary instrument for monitoring organic compound concentrations in air and other gases and gas mixtures. Recently, it was also employed as the detector of choice in Supercritical Fluid Chromatograph (SFC) instruments.

Traditionally, the FID is based on a hydrogen diffusion flame where a hydrocarbon free (zero grade) hydrogen gas is fed through a flame tip (jet) surrounded by a coaxially much higher flow of purified (zero grade) air. Typically, helium gas is also added to the central hydrogen flow, as a make up gas to further enhance the performance of FID as a GC detector. Examples of the gas flow rates are: 30 ml/min hydrogen, 30 ml/min helium and 300–400 ml/min air.

The operation of an FID is based on $H_2/O_2$ combustion decomposition of organic compounds, while forming some CH radicals, followed by the flame chemical ionization reaction $CH+O \rightarrow CHO^+ + e^{31}$. The emerging flame induced current is then measured and it is proportional to the flux of organic compounds over 5–7 decades linear dynamic range. Typical flame chemical ionization yield is 15 milliCoulomb per gram carbon. The ionization response is selective to carbon atoms only and is generally uniform among the organic compounds, however, secondary molecular effects exist and $CO$, $CO_2$, $CS_2$ are practically undetectable while certain hetero atoms, such as organo oxygen or nitrogen, reduce the carbon detection in those compounds. While the vast majority of FID's are operated with air, some studies have been performed with pure oxygen instead of air in the hydrogen diffusion flame and a very limited number of investigators have studied the effect of gas composition in premixed hydrogen air flames. FID operated with premixed $H_2/O_2$ alone is not used, probably due to the danger of flashbacks and penetration of the flame through the flame tip to the gas source in an unsafe or controlled way. Hence, the hydrogen diffusion FID became the GC industry standard detector of choice due to its sensitivity, carbon selectivity, large linear dynamic range and simple and robust operation.

In spite of the above-described desirable features, the FID suffers from one major disadvantage, which is a large gas consumption. This results in several undesirable features:

1) High cost of gases.
2) High cost of instrumentation and installation.
3) Low safety, since a compressed hydrogen gas cylinder is a major hazard in the laboratory, as this gas is flammable and liable to explode in air.
4) High weight and large size of the instrument, due to the gas cylinders or sources.

Recently, there is a growing use of hydrogen and zero grade air generators. Hydrogen is generated through the electrolysis of water and then separated from the co-generated oxygen by a polymeric or palladium membrane and compressed to a stabilized pressure of several atmospheres, as well as passing final stages of purification before the usual delivery into the GC. Room air is compressed to the usual delivery pressure by a mechanical compressor and then its hydrocarbon residual content is removed to a low acceptable level, usually through catalytic combustion, such as on a heated platinum wire. Again, the available instrumentation is expensive, bulky and requires excessive maintenance.

In a conventional water electrolysis, water is electrochemically separated into hydrogen and oxygen gases. While for general use in a hydrogen generator, the hydrogen must be separated, purified and compressed, it has been discovered that for FID usage, no such separation and purification is required and a premixed (stoichiometric) $H_2/O_2$ gas composition mixture can be used. In addition, the FID imposes no gas conductance barrier, thus only a few millibar pressure difference in the electrolyser is enough to drive the gas mixture to the detector. In other words, it has been found that FID can be powered by a simple water electrolysis that, in contrast to the conventionally used hydrogen and zero air generators, is characterized by the following characteristics:

1. The hydrogen gas generated is not thoroughly cleaned or separated from the oxygen;
2. Oxygen is provided to the flame instead of air;
3. Oxygen is provided to the flame from a water electrolyser instead of air;
4. The FID can be powered by premixed $H_2/O_2$ gases instead of the commonly used hydrogen diffusion air flame;
5. Water vapor are only partially removed, since without condensation the vapor is harmless to the flame;
6. The electrolysis generated gases do not have to be compressed and pressure stabilized. In fact, the total gas flow rate is controlled by the electrolysis current that acts as an electronic flow control, creating a small driving pressure gradient;
7. The water electrolysis provides "zero grade" gases without hydrocarbon impurities;
8. A relatively low total combustible gas flow rate can sustain a stable flame, and
9. The FID can be powered by a near stoichiometric $H_2/O_2$ gas mixture.

The present invention is based on the replacement of air and hydrogen cylinders or separate hydrogen and air generators, with a very simple water electrolyser which provides an unseparated (stoichiometric) $H_2/O_2$ gas mixture. Accordingly, the hydrogen diffusion flame with air is replaced by a premixed near stoichiometric $H_2/O_2$ flame, where advantageously the flame source and gas line are structured to prevent flame flashbacks.

Electrolyser powered FID (EFID) of the present invention possesses the following main advantages: 1. Reduced cost of operation. The price of distilled water is negligible compared to that of the gases it replaces, while the cost of this simple electrolyser is much lower than the conventional hydrogen and zero grade air generators or empty gas cylinders and their pressure regulators, gas valves, tubes and pneumatics involved and the safety requirements of hydrogen handling. 2. The EFID is safer. No compressed hydrogen (and air) is required and only a few millileter of combustible gas mixture is stored at any time. The total combustible gas flow rate is also much smaller and thus, even if uncombusted, this mixture is easily diluted in air to a safe unignitable diluted level. 3. Independent total gas supply. The EFID can be operated with automatic water introduction while eliminating the dependency on external gas sources and its shipment, storage and cylinder exchange.

In total organic compound analysis in air, the partial air pressure or presence of hydrogen does not affect the results, since the air sample is a small part of the electrolyser $H_2/O_2$ gas mixture, in contrast to a conventional FID in which the air supplied contains both the sample, as well as the required oxygen. 4. Improved sensitivity. The EFID is inherently operated with "zero grade" gases without any hydrocarbon impurities. Thus, its noise level is usually lower that that of FID. When operated at a relatively high combustible gas mixture flow rate, its chemical ionization yield is higher than that of FID. These two aspects combined enable a higher sensitivity of the EFID, and 5. Enhanced portability. The EFID provides the ultimate in FID portability. The electrolyser according to the invention weighs only about 450 grams and consumes much less energy (and water) than its alternatives. Also, it does not require a license for transporting compressed hydrogen.

It is therefore a broad object of the present invention to provide an improved method for producing a flame for analysing a sample by flame ionization.

It is a further object of the invention to provide an improved detection apparatus for producing a flame for analysing a sample by flame ionization.

According to the present invention there is provided a flame based method for analyzing a sample by introducing the sample into a combustible gas mixture, igniting the combustible gas mixture to produce a flame, and detecting a characteristic of the resulting flame to determine the identity and/or concentration of one or more chemical substances in the sample, characterized in that said combustible gas mixture is generated by water electrolysis.

The invention further provides a flame ionization method of analyzing a sample by introducing the sample into a hydrogen and oxygen (or air) flame and detecting the charge carriers produced by the combustion of organic matter in that flame, to determine the identity and or concentration of one or more chemical compounds in the sample, characterized in that said flame is produced by gases generated from water electrolysis.

The invention also provides a flame based detector apparatus for analyzing a sample in order to determine the identity and/or concentration of one or more chemical substances therein, comprising inlet means for introducing combustible gases therein, feeding means for introducing the sample into said combustible gases, ignitor means for igniting the combustible gases to produce a flame and detector means for detecting a characteristic of the resulting flame to determine the identity and/or concentration of one or more chemical substances in the sample, and water electrolyser means for generating said combustible gases and for directing the gases to said inlet means.

The invention will now be described in connection with certain preferred embodiments with reference to the following illustrative figures so that it may be more fully understood.

With specific reference now to the figures in detail, it is stressed that the particulars shown are by way of example and for purposes of illustrative discussion of the preferred embodiments of the present invention only and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the Drawings:

FIG. 2 are chromatograms of a conventional FID and an EFID according to the invention;

Figure 1:
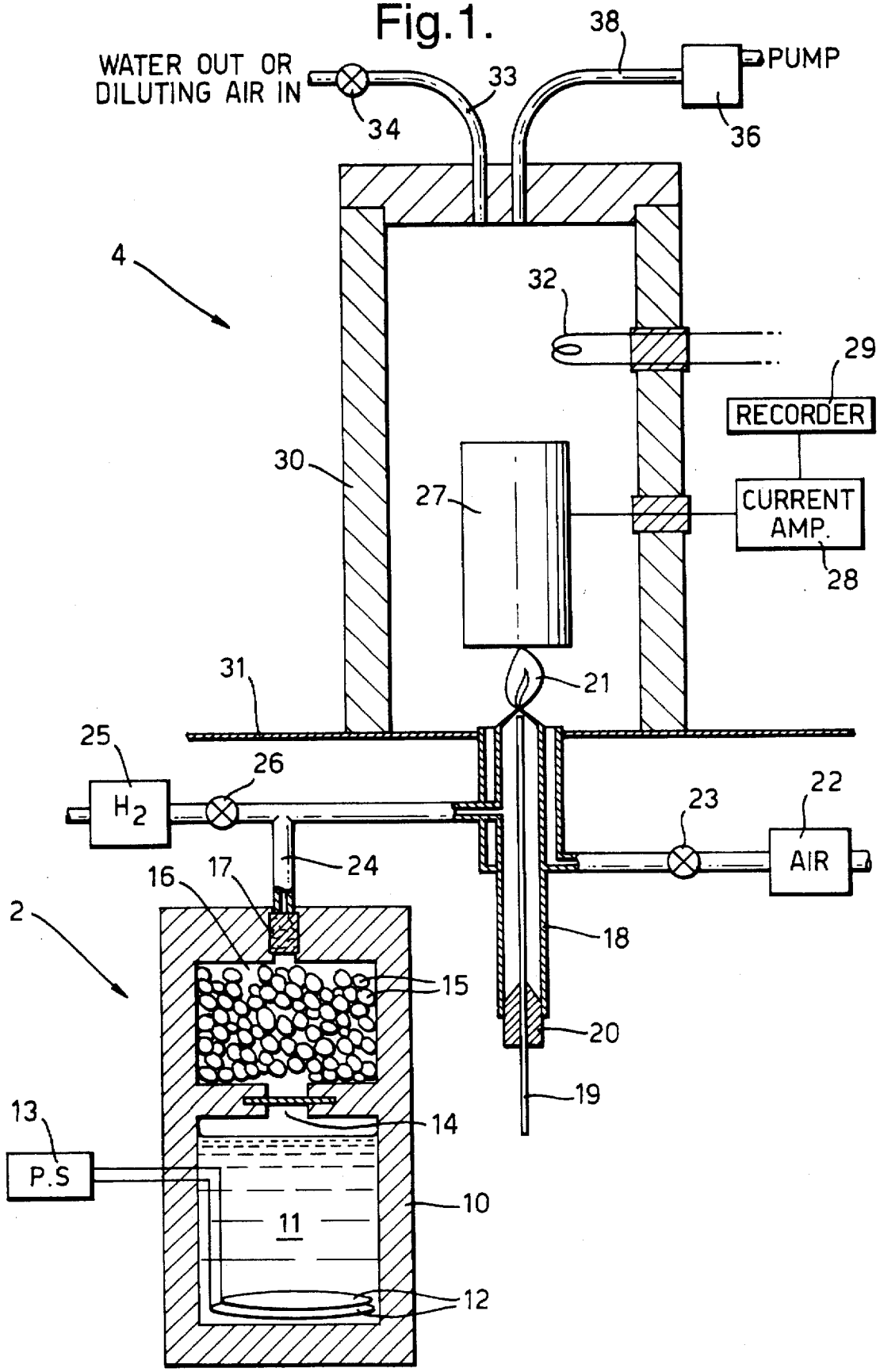
FIG. 1 is a schematic, cross-sectional view of an electrolyser powered flame ionization detector according to the present invention.

The EFID according to the present invention is composed of two portions of a water electrolyser 2 and an FID 4. The water electrolyser 2 consists of a container 10 for holding water 11 with KOH (typically 1 molar concentration) and two nickel mesh electrodes 12 connected to an external power supply 13 by means of electrical wires. The generated $H_2/O_2$ gas mixture passes through a membrane 14, e.g., a teflon membrane, for partial separation from water mist. The gas mixture is further dried by silica gel drying material 15 disposed in a chamber 16 on the other side of the membrane 14. The dryed gas mixture is passed through a frit flow restrictor 17 to a flame source in the form of a conduit 18. Inside the conduit 18 there is disposed a column or a tube 19 for directing a sample of GC effluent or external air to the upper edge of the conduit 18. The tube 19 is sealed inside the conduit 18 by a seal 20. Hence, the $H_2/O2$ gas mixture is directed to the upper open edge of the conduit 18 where it mixes with the sample gas flowing through the tube 19 and feeds a flame 21. The flame can be surrounded by auxiliary air directed thereto from a source 22, via a control valve 23. The conduit 24 directing the flow of dryed gas to tube 18, is also connected to a source of hydrogen 25, the flow of which to the conduit 24 is controlled by a valve 26. When both valves 23 and 26 are opened, while the electrolyser 2 is off, the electrolyser FID (EFID) is converted to an FID.

Charged carriers produced by the flame 21 are collected by a collector electrode 27 biased by a typical voltage of −200V. The thusly produced current is amplified by amplifier 28 and the amplified signal can then be further processed and displayed by a computer or recording device 29. The flame 21 and collector electrode 27 are protected by an electrical and wind shield 30 mounted on a base 31. There is also provided a flame ignitor 32, water exit tube 33, controlled by valve 34, and an air pump 36 communicating with the interior of the shield 30 by means of a pipe 38. When the EFID is used as an air analyser, the air pump 36 is activated, tube 19 is open to the air and valve 23 is partially opened to allow external air sampling. Alternatively, valve 23 can be partially or fully opened, allowing the addition of diluting external air to the flame, in addition to the electrolyser's gases. This additional air is sometimes desirable for reducing water condensation or for preventing flame quenching by a large amount of hydrocarbon eluting from the GC.

The water electrolyser 2 may have the dimensions of 66 mm diameter and 112 mm long, very similar in its dimensions to a standard beverage can. Its lower volume contains up to 120 ml water with 7 grams of KOH added to increase the water conductivity. The two round pieces of nickel mesh electrodes 12 are electrically separated at the bottom of the container, serving for the actual water electrolysis. These meshes are connected to a standard power supply operated typically at 2.6 Volt, 1.5 Ampere with total power consumption of 4 Watts. Under these conditions, about 18 ml/min of stoichiometric $H_2/O_2$ gas mixture is formed. The gas mixture passes through an upper teflon membrane 14, separating the water mist formed by the gas bubbles during the electrolysis. The gas mixture is further passed through a water drying material 15, typically silica gel. The volume of the drying material is calculated to be just enough for the water treated below, and is replaced or redried in an oven at each water addition cycle. The 120 ml water enables about 100 ml water consumption. At 1.5 Ampere, the water consumption is 12 ml/day, thus this relatively small electrolyser provides the total gas consumption of the EFID for over a week and at 1 Ampere it can even last for 12 days. A larger water electrolyser with up to 1 liter water volume and having a separate dripping chamber and drying material tube, may continuously operate close to 3 months. The $H_2/O_2$ unseparated mixture flows through a frit flow restrictor element 17, e.g., a 100 ml/min standard element. This frit element has a dual purpose: it acts as a flame arrestor to ensure the safety of the electrolyser, so as to eliminate a possible danger of flame flashback into the electrolyser. In addition, the frit element builds a low pressure of a fraction of an atmosphere in the electrolyser, helping to stabilize the output flow rate of the electrolyser. The FID 4 is a standard FID modified to increase the heat transfer from the base 31 to the charge collector, in order to avoid water condensation, which presents a problem due to the lack of high flow rate of diluting air which is conventionally used. The sample to be analyzed is fed from the GC tube 19 ending near the flame 21. The sample is swept by the $H_2/O_2$ gas mixture into the flame where it is combusted to form electric current as in a conventional FID. In the analysis of total organic compound in air, the sample can be fed either from an additional co-axial air flow or through the tube with prior mixing with the combustible gas mixture. It was found that the flow of the $H_2/O_2$ gases through the flame is sufficient to act as a Ventury pump inducing a flow of external air through a short central tube. Thus, when the tube is properly adjusted, an air pump is not essential for the measurement of total organic compounds in air. The EFID structure should, however, be thermally insulated to avoid water condensation if it is heated only by the flame.

The charged particles which are produced are collected in the normal way by the electrically biased collector 27 and is recorded versus time. In other FID structures, the source of the flame is biased while the collector is directly connected to the current amplifier. The source of the flame in the FID according to the present invention is narrower than usual, since it emanates from a hole having a diameter of 250 µto ensure the lack of flashbacks, as the flame cannot propagate back through a small hole of a diameter such as 250 µ. No external hydrogen, air or helium is used except the normal column flow of helium or nitrogen. In the event hydrogen is used as a carrier gas, the flame becomes slightly hydrogen rich without any major perturbation.

Referring to FIG. 2, there is illustrated a comparison between chromatograms obtained with a conventional FID and according to the present invention, with an EFID. For the purpose of the comparison there has been used a 0.2 µL solution of methanol a having 20 ppm (volume) concentration of toluene b, octane c, xylene d and nonane e, injected into a 6 meter long capillary column with 0.2 mm ID, having 1 ml/min helium carrier gas flow rate. The 0.2 µL sample was split 100 times and in consideration of the specific gravity of the compounds, about 35 picogram of each molecules b to e was analyzed. Thus, this typical chromatograph of toluene, octane, xylene and decane at a 20 ppm concentration level in methanol (volume), was obtained by injecting about 35 picograms of each into a 6 meter narrowbore (0.20 mm ID) tube 19. It is seen that both the amplifier noise background and ionization yield are similar in the EFID in comparison with the conventional FID. The EFID ionization yield is about linearly increased with the total gas flow or electrolyser's current used, but this yield increase may also involve a higher background noise. A careful comparison of the EFID chromatograph to the FID chromatograph reveals that the relative ionization yield of toluene and xylene compounds is slightly increased, while that of the aliphatic compounds octane and nonane is slightly reduced. This is interpreted as the result of the premixed stoichiometric composition. It was found that if hydrogen is used as a carrier gas, or the gas mixture is enriched with hydrogen through a selective oxygen depletion, this phenomenon is reduced in its magnitude.

Figure 3A:
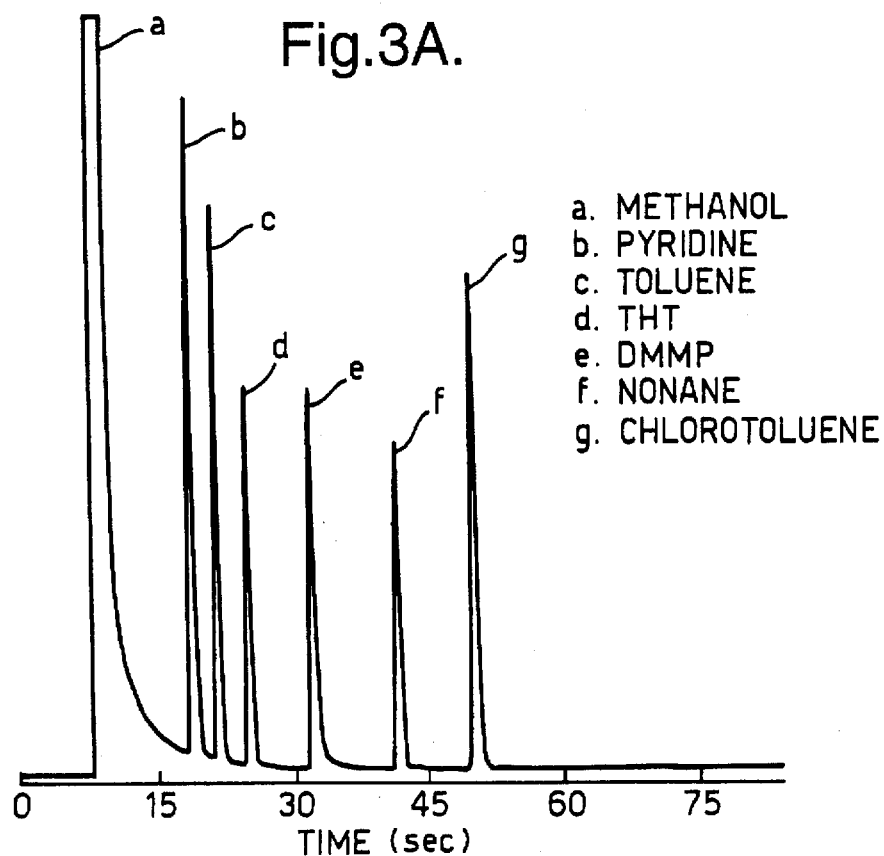
FIG. 3 are further chromatograms obtained by using different compounds with a conventional FID and an EFID according to the present invention.
Figure 3B:
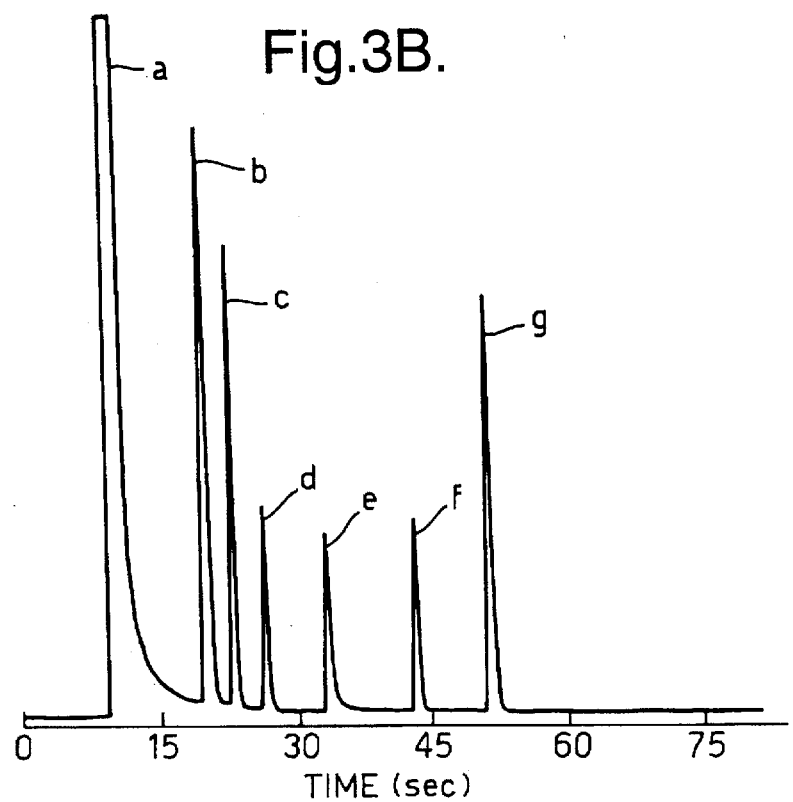

An additional comparison between a conventional FID and an EFID according to the present invention is shown in FIG. 3. Here, a 0.2 µL solution of methanol with the indicated compounds at $10^{-3}$ volume concentration was injected to the column as described with reference to FIG. 2 and with the same split ratio of 100.

The comparison of EFID and FID chromatograms of compounds with N,S,P,Cl heteroatoms shows that with the exception of minor relative intensity increase of the aromatic compounds (see FIG. 2), the traces are very similar. Thus, it is seen that in spite of the major differences in the gas composition, the EFID is similar to FID in its operational characteristics as a carbon selective detector with about uniform carbon response and having a similar sensitivity. Also, the FID chromatogram was achieved with zero grade gases producing only 3 picoAmpere background current. When less clean gases are used, the FID noise level is increased while the electrolyser always produces "zero grade" $H_2/O_2$ mixture. A minor problem may exist with the EFID in that a possible flame blow-off may occur when a large amount of solvent is eluted. With normal use of a narrowbore tube (column), this problem does not exist, but with splitless injections of over one microlite solvent into bigger tubes (columns), this problem may exist and can be solved by the addition of coaxial air flow at a low flow rate. This coaxial air flow can be provided by a miniature pump operated only during the solvent elution time and by using room air. Alternatively the flame can be sensed through its background current, followed by an automatic reignition.

Figure 4:
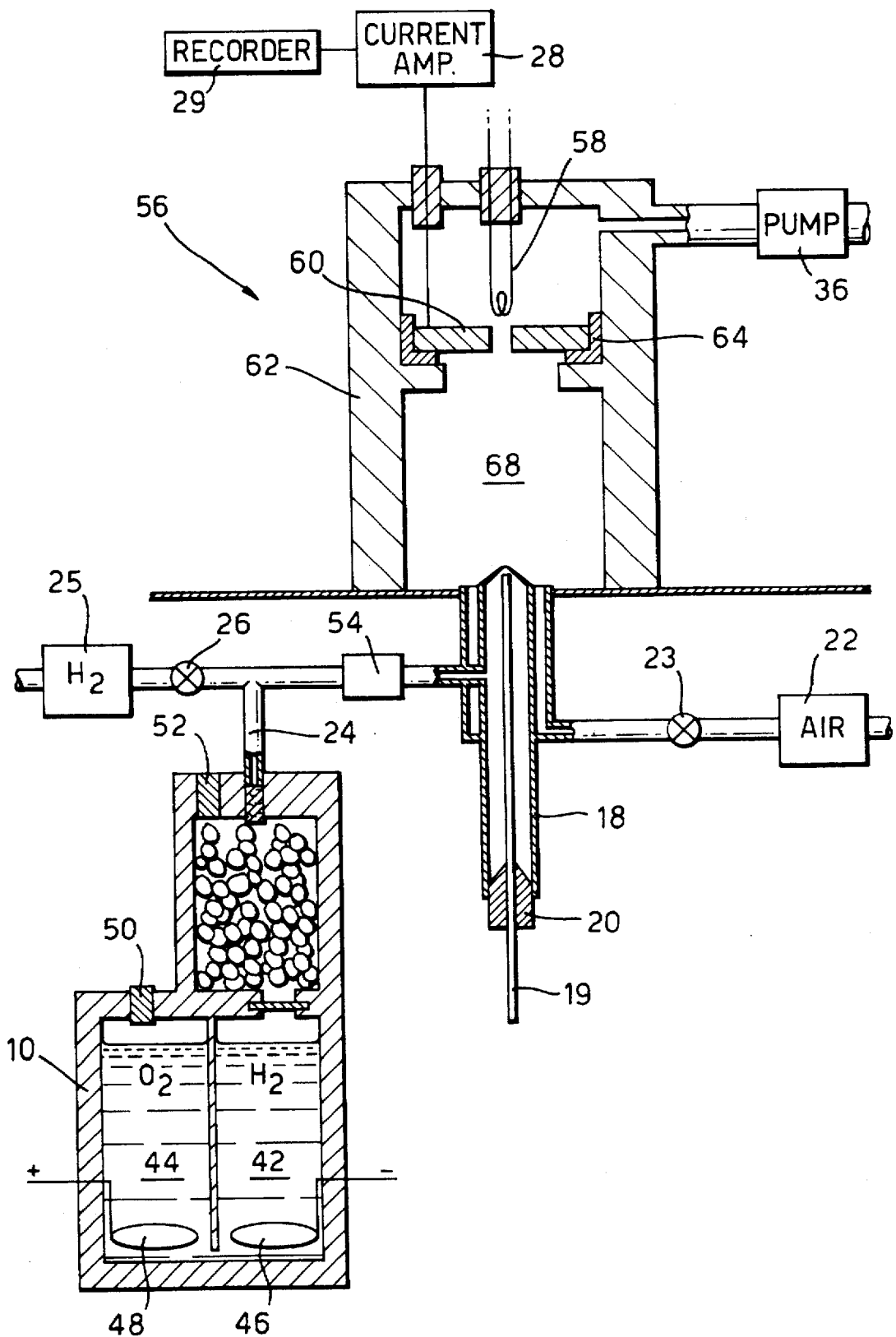
FIG. 4 is another embodiment of an EFID according to the present invention.

Turning to FIG. 4, there is shown another embodiment of the invention of an Electrolyzer powered Pulsed FID (EPFID). A pulsed flame is a flame which, once ignited, propagates to the gas source and self-terminates. It can then be reignited periodically or triggered in an external manner. According to this embodiment the container 10 of the electrolyser 2 is divided by a partition 40 into two chambers 42 and 44, which chambers are in fluid communication with each other. In each chamber there is located an electrode 46, 48 forming a hydrogen generating cathode side and an oxygen generating anode side. Each side is provided with a pressure releasing frit 50, 52 and/or a check valve, in order to minimize pressure difference between the two sides. Such an electrolyser produces a hydrogen rich gas mixture to allow a larger amount of air to be sampled. On the conduit 24 there is introduced a solenoid valve 54 for effecting the introduction of the gases into the FID 56 in a pulsed manner. The pulsed FID is built as a closed pulsed flame combustion cell having an ignitor 58 positioned thereabove for easy repetitive ignition. As seen, the structure of the charge collector 60 is configured as a disc, and is mounted in the shield 62 by means of an insulator 64.

While the embodiment of FIG. 4 was described as an embodiment suitable for use as an EPFID, it should be noted that both electrolysers shown in FIGS. 1 and 4 can be operated as EFID or EPFID.

The ignited flame propagates in the chamber and consumes the $H_2/O_2$ gas mixture until its extinction, since it cannot propagate through the narrow diameter gas entrance. The continuous gas flow expels the combusted water until fresh combustible gas mixture arrives at the igniter for reignition. The ions formed in the pulsed flame are collected and detected either in the usual way, or with a gated amplifier or AC-DC conversion system, such as an electronic peak detecting system. The EPFID offers several advantages, especially for a field portable FID, in the measurement of total hydrocarbon in air, or other gases or in the detection of leaks of organic compounds:

A) The power and water consumption, as well as total weight of the EPFID, can be smaller than EFID. Since the flame is unstable, no minimal "holding" current or gas flow rate is required and the power and water consumption can be arbitrarily reduced, depending on the response time required. The PEFID can be operated at 15 Hz when 1.5 Ampere is used (depending on the chamber's volume). If the igniter is pulsed, such as with the use of spark ignition, a 0.1 Ampere can be used with 1 Hz PEFID operation and about 1 second response time. Alternatively, the gas mixture can be released by means of a solenoid valve synchronized with the pulsed ignition. An important feature of this mode of operation is that the air can be pumped continuously, thus carrying with it substantially all the water formed by the pulsed flame without any need for heating. This elimination of the need to heat the detector, reduces the EPFID power consumption. The continuous air pumping with a low compression ratio pump, such as a small conventional electronic cooling fan, also helps to trap condensable organic compounds for increased sensitivity. The preferred mode of EPFID operation is with pulses of hydrogen rich gas mixture mixed with sampled air and pulsed ignition.

B) No flame extinction problems exist with the EPFID, since solvent induced flame extinguishing is automatically cured due to the continuous flame ignition in the EPFID. When the solvent is fully eluted and discharged from the detector, the EPFID pulsed flame is automatically and repeatedly reignited.

While the major use of the electrolyser powered flame, described herein is for flame ionization detection, other flame based detectors can also benefit from the gas mixture provided by the water electrolyser. Most notable is the Nitrogen Phosphorus Detector (NPD). The NPD is another popular GC detector. It is based on a partial combustion of the sample compounds with low hydrogen flow rate of 3–4 ml/min and FID like co-axial flow of air around an electrically heated bead. Organo phosphorus or nitrogen compounds are pyrolyzed and form negative $CN^-$ and $PO^-_2$ ions at the surface of the bead that produces the detected current. The water electrolyzer of the EFID can provide a low flow rate of $H_2/O_2$ mixture instead of the pure hydrogen used and thus, eliminate the need for a pure hydrogen source and its delicate low flow rate stabilization.

Figure 5:
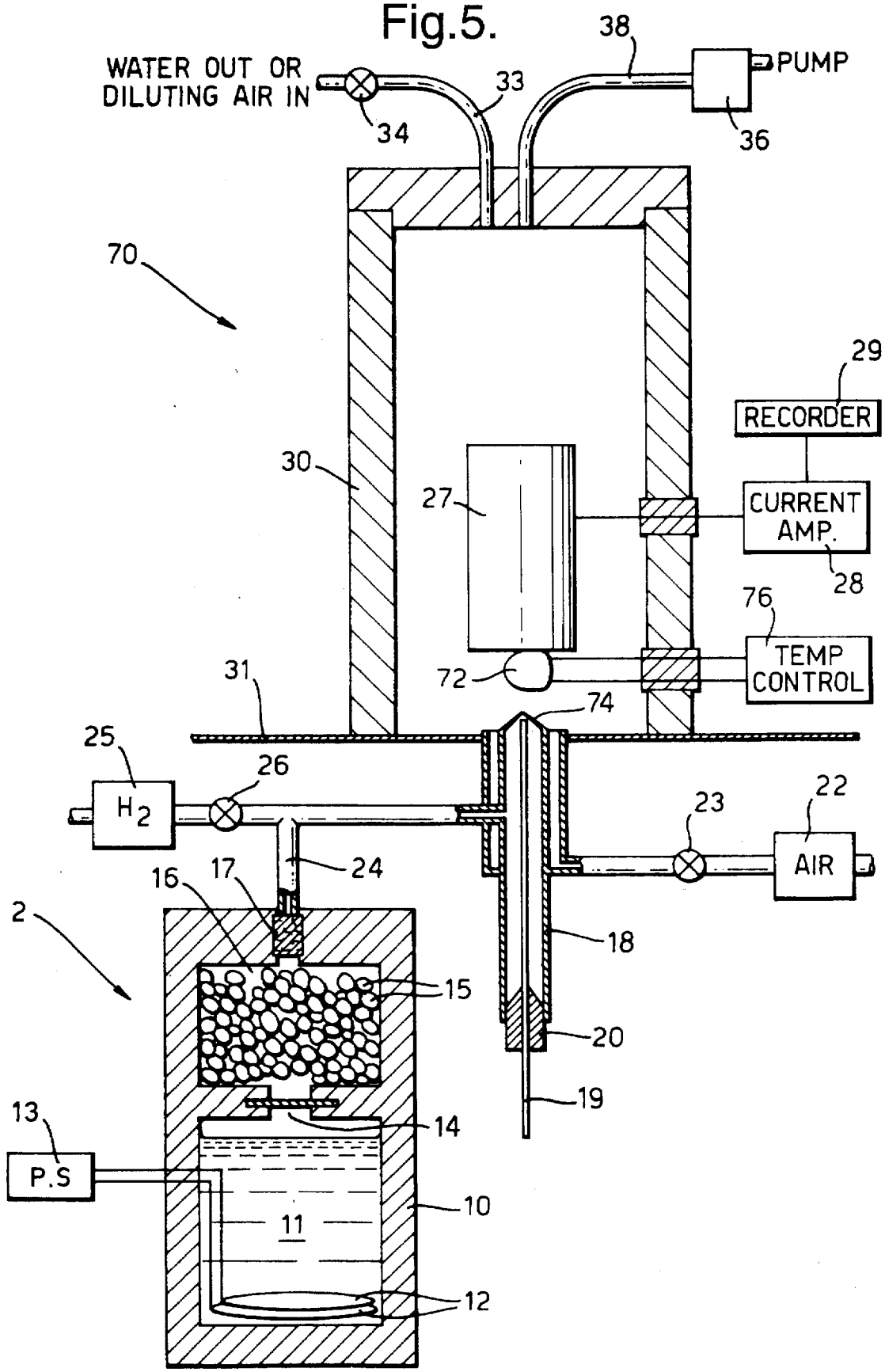
FIG. 5 is a cross-sectional view of an electrolyser powered nitrogen phosphorous detector according to the present invention.

The electrolyzer powered (NPD) (ENPD) is schematically illustrated in FIG. 5. As shown, the ENPD is similar to the EFID of FIG. 1 with the difference that the FID portion is replaced by an NPD structure. The NPD structure 70 comprises a ceramic bead 72, disposed above the combustible gas source 74 and being electrically heated and thermally controlled by controller 76. Typical bead temperatures are 600°–800° C., and thus the bead also replaces the flame igniter. Electrolyzer 2 provides a low flow rate (i.e., 6 ml/min) of hydrogen and oxygen gas mixture that is further diluted with the air that is introduced and flow regulated by valve 23. The sample compounds are mixed with the electrolyzer produced gases and pyrolyzed due to their partial combustion in the usual manner on the bead to produce the negatively charged ions from nitrogen or phosphorus containing compounds. The bead is usually biased at a negative potential to repel negative ions while the gas source 74 can either be grounded or biased at a low positive potential (phosphorus detection) or negative potential (nitrogen detection). Actually, today in most GCs that have an NPD an FID is also mounted, and thus, the same electrolyzer used for the EFID could be used for ENPD with the great benefit of removal of the pure hydrogen source from the laboratory.

The electrolyzed powered flame can also be used in several other flame based detectors. Most important are the flame based detectors that produce simpler species that are amenable for easier detection by other means including:

1) $SO_2$ formation from sulfur compounds for their detection via lamp induced fluorescence.

2) $SO_2$ formation from sulfur compounds for their further reduction to SO followed by ozone induced chemiluminescence detection. Here the EFID is used in tandam with a consecutive sulfur selective detection. The low total flow rate of the EFID is important for optimal ozone chemiluminescence detection and it forms only water that is easy to pump, thus, the vacuum pumping capacity of this detector is reduced.

3) NO can be formed at the electrolyzer powered flame from nitrogen compounds and be further detected by ozone induced chemiluminescence or photo ionization.

4) Metal atoms can be produced by the electrolyzer powered flame for their detection by the atomic absorption or fluoresence methods, or simply by their flame chemiluminescence emission. Thus, an electrolyzer powered flame photometer detector can be used for metal, and especially for alkali metal detection in water and biofluids.

It will be evident to those skilled in the art that the invention is not limited to the details of the foregoing illustrated embodiments and that the present invention may be embodied in other specific forms without departing from the spirit or essential attributes thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed is:

1. A flame based method for analyzing a sample by introducing the sample into an enclosure including a combustible gas mixture, comprising the steps of:

generating by means of a water electrolyser a premixed hydrogen and oxygen gas mixture, said water electrolyser being capable of providing the gas mixture require for solely sustaining a flame;

stabilizing the output flow rate of said premixed gas mixture for reducing the flame background noise;

heating said enclosure to a temperature sufficient for preventing water condensation in said enclosure;

feeding said mixture via a flame source having an opening sufficiently small for preventing a flame flashback towards said electrolyser;

igniting said gas mixture to produce a flame, and detecting a characteristic of the resulting flame to determine the identity and/or concentration of one or more chemical substances in the sample.

2. The method according to claim 1, wherein the water generated premixed combustible gas mixture is a nearly stoichiometric hydrogen and oxygen gas mixture.

3. The method according to claim 1, wherein the gas mixture is enriched with another gas or gas mixture.

4. The method according to claim 1, wherein the hydrogen and oxygen gas mixture is enriched with hydrogen.

5. The method according to claim 1, wherein said gas mixture is directed to a detector at approximately atmospheric pressure without compression and pressure stabilization.

6. The method according to claim 1, wherein said sample is mixed with said gas mixture prior to reaching the flame.

7. The method according to claim 1, wherein said sample is fed to the flame by means of air flowing around the flame.

8. The method according to claim 1, wherein said sample is eluted with a carrier gas from a column of a gas chromatograph.

9. The method according to claim 8, wherein said carrier gas of the gas chromatograph is hydrogen or air.

10. The method according to claim 1, wherein said sample is an organic compound in air or another gas or gas mixture.

11. The method according to claim 1, wherein additional coaxial flow of air or oxygen is directed around the flame to prevent flame extinction by a large amount of hydrocarbon and/or to eliminate water condensation.

12. The method according to claim 11, wherein said additional coaxial flow of air is provided by a small air pump from the surrounding room or outdoor air.

13. The method according to claim 1, wherein the flame is a conventional continuously lit flame.

14. The method according to claim 1, wherein the flame is a pulsed flame.

15. The method according to claim 1, wherein the flame produced characteristic is a negative ion species produced on a nitrogen phosphorus detector bead.

16. The method according to claim 1, wherein said flame characteristic is charged carriers produced by the flame from said sample.

17. The method according to claim 16, wherein the flame is operated as a conventional flame of a flame ionization detector with a hydrogen diffusion air flame.

18. A flame based detector apparatus for analyzing a sample in order to determine the identity and/or concentration of one or more chemical substances therein, comprising:

a flame ionization detector including an enclosure having an inlet means;

water electrolyser means for generating a premixed hydrogen and oxygen gas mixture and for directing the gas mixture to said inlet means, said water electrolyser being capable of providing the gas mixture required for solely sustaining a flame;

means for stabilizing the output flow rate of said premixed gas mixture for reducing the flame background noise;

flame feeding means, including a flame source having an opening sufficiently small for preventing a flame flashback towards said electrolyser;

heating means for heating said enclosure to a temperature sufficient for preventing water condensation in said enclosure;

ignitor means for igniting the gas mixture to produce a flame, and detector means for detecting charged carriers produced by the flame from said sample for determining the identity and/or concentration of one or more chemical substances in the sample.

19. The detector apparatus according to claim 8, wherein said premixed gas mixture is fed to the flame coaxially with said feeding means for introducing the sample.

20. The detector apparatus according to claim 18, further comprising means for directing air or oxygen around the flame.

21. The detector apparatus according to claim 18, further comprising a ceramic bead disposed above said feeding means and being electrically connected to a temperature controller.

* * * * *